Figure 1:
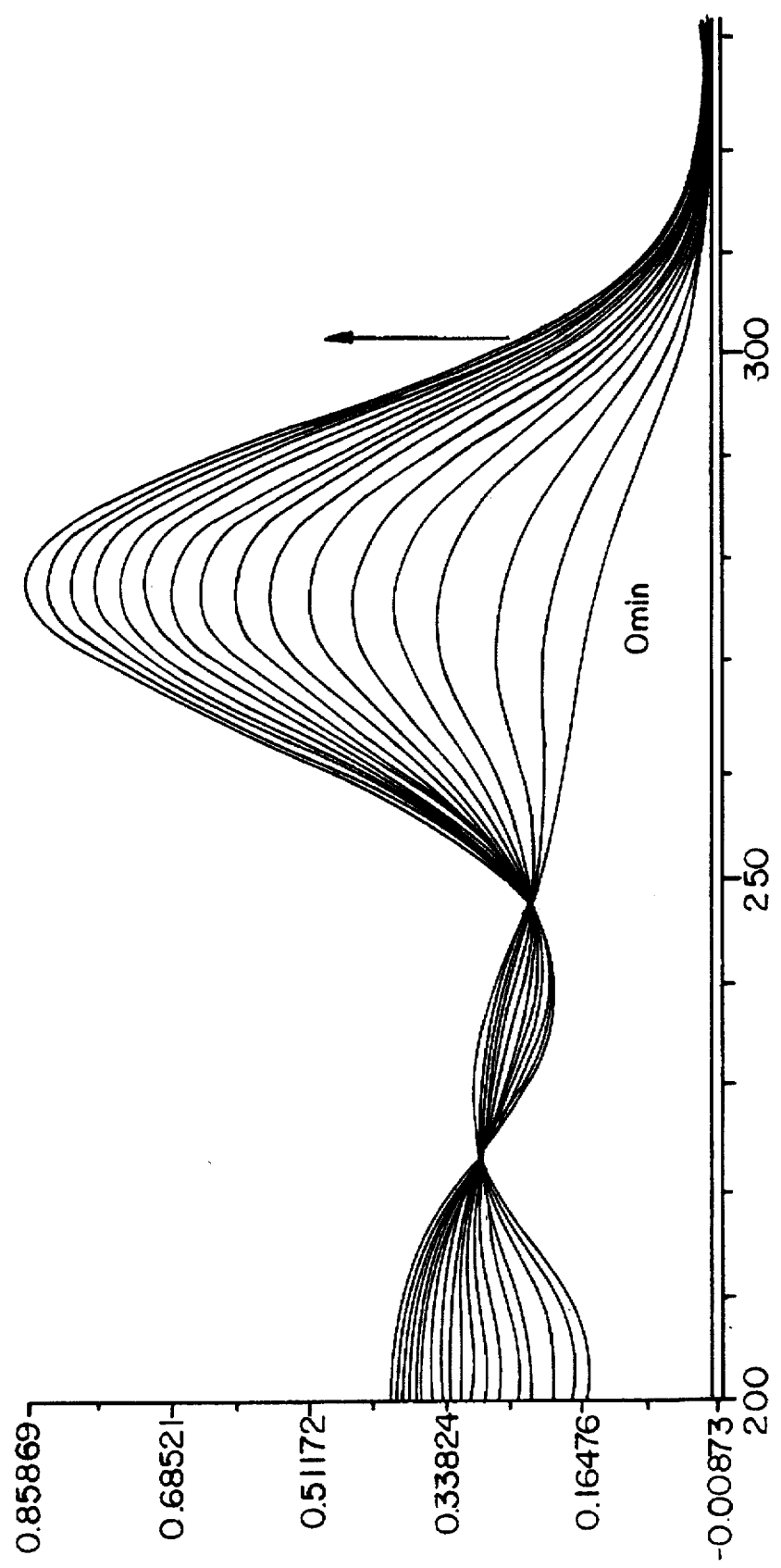

United States Patent [19]

Geczy et al.

[11] Patent Number: 5,698,535
[45] Date of Patent: Dec. 16, 1997

[54] SIN-1A CYCLODEXTRIN INCLUSION COMPLEXES

[75] Inventors: Joseph Geczy, Brussels, Belgium; Andrasne Vikmon, Budapest, Hungary; Jozsef Szejtli, Budapest, Hungary; Lajos Szente, Budapest, Hungary; Julianna Szeman, Budapest, Hungary

[73] Assignee: Therabel Industries, S.A., La Seyne-Sur-Mer, France

[21] Appl. No.: 571,853

[22] PCT Filed: Apr. 25, 1995

[86] PCT No.: PCT/HU95/00011

§ 371 Date: Apr. 16, 1996

§ 102(e) Date: Apr. 16, 1996

[87] PCT Pub. No.: WO95/29172

PCT Pub. Date: Nov. 2, 1995

[30] Foreign Application Priority Data

Apr. 26, 1994 [HU] Hungary .................. HUP9401183

[51] Int. Cl.$^6$ .................. A61K 31/715; C08B 30/18; C07D 271/02

[52] U.S. Cl. .................. 514/58; 536/46; 536/103; 514/46; 424/464; 424/499; 548/125

[58] Field of Search .................. 536/46, 103; 514/58; 424/464, 499; 548/125

[56] References Cited

U.S. PATENT DOCUMENTS

| | | | |
|---|---|---|---|
| 5,039,705 | 8/1991 | Keefer et al. | 514/611 |
| 5,208,233 | 5/1993 | Keefer et al. | 514/231.8 |
| 5,212,204 | 5/1993 | Keefer et al. | 514/647 |
| 5,298,496 | 3/1994 | Vikmon et al. | 514/58 |
| 5,366,997 | 11/1994 | Keefer et al. | 514/611 |
| 5,389,675 | 2/1995 | Christodoulou et al. | 514/492 |

OTHER PUBLICATIONS

On the Mechanism of NO Release from Sydnonimines, Feelisch, M. et al. J. Cardiovascular Pharmacology 14(Suppl. 11)S13–S22 (1989).

Oxygen and Oxidation Promote the Release of Nitric Oxide from Sydnonomines, Bohn, H. et al., J. Cardiovascular Pharmacology 14(Suppl. 11) S6–S12 (1989).

Primary Examiner—John Kight
Assistant Examiner—L. Eric Crane
Attorney, Agent, or Firm—Steinberg, Raskin & Davidson,P.C.

[57] ABSTRACT

New inclusion complexes which are stable in their so-lid state formed of SIN-1A and cyclodextrins or cyclodextrin derivatives and optionally also containing ions as catalyst or stabilizer. The complexes release nitric oxide at room temperature upon dissolving in water or aqueous systems. The ions are preferably carboxylic acid anions such as acetate, formiate, propionate, ascorbinate, tartarate and/or lactate and/or inorganic acid anions such as phosphate, phosphite, borate, carbonate, hydrocarbonate, sulfate, sulfite and/or cations such as alkali and/or ammonium.

Pharmaceutical compositions as well as kits containing the complexes. The kits are to be used as NO-liberating standards to release NO in a predictable amount and rate on dissolving in aqueous media.

Processes for the preparation of the complexes by subjecting at a suitable pH SIN-1 to the catalytic action of ions to shift the equilibrium towards formation of SIN-1A in the presence of cyclodextrins or cyclodextrin derivatives capable to form inclusion complexes, whereby the SIN-1A formed is immediately complexed and stabilized and isolating in the solid state the obtained new complexes optionally containing ions.

A preferred process includes reacting SIN-1 and a cyclodextrin or cyclodextrin derivative in the solid state in the presence of a salt as a catalyst by thoroughly admixing or milling the components together or by freeze drying an aqueous, oxygen-free solution containing the components, followed preferably by "second drying" in vacuo.

19 Claims, 2 Drawing Sheets

SIN-1A CYCLODEXTRIN INCLUSION COMPLEXES

The invention relates to physiologically active nitric oxide releasing agents, processes for preparation thereof, compositions containing as well as methods to use the same.

More particularly the invention relates to new SIN-1A inclusion complexes which are stable in their solid state and which are formed with cyclodextrins or with cyclodextrin derivatives and which are releasing nitric oxide at room temperature upon dissolving in water or aqueous systems and which optionally also contain ions as catalyst or stabilizer. The invention also relates to processes for their preparation, compositions containing the same and methods for their use.

The following abbreviations are used in this specification:

| | |
|---|---|
| SIN-1 | 3-morpholino-sydnonimine |
| SIN-1A | N-morpholino-N-nitrosoaminoacetonitrile |
| SIN-1C | cyanomethylene-amino-morpholine |
| CDPSI | ionic soluble β-cyclodextrin polymer |
| DIMEB | heptakis-2,6-di-O-methyl-β-cyclodextrin |
| EDRF | endothelium- derived relaxing factor |
| HPβCD | hydroxypropyl-β-cyclodextrin 2,8 hydroxypropyl group per CD-unit (average) |
| Molsidomin | N-ethoxycarbonyl-3-morpholino-sydnonimine |
| RAMEB | randomly methylated-βCD, ≈ 12 methoxyl group per CD-unit (average) |
| TRIMEB | heptakis 2,3,6-tri-O-methyl-β-cyclodextrin. |

It is known, that nitrogen monoxide may have a reduced form (NO•) which is designated as nitric oxide, and an oxidized form (NO$^+$) which is called nitrosonium ion. Nitric oxide (NO•) is implicated in numerous important bioregulatory processes.

The utility of a NO releasing donor depends on both the depth and duration of the mean arterial pressure lowering effect. Longer acting NO-donors are needed, which release the NO without metabolic transformation of the donors, i.e. which are not depending on the liver functions. Furthermore, a NO-donor should have some lipophilic character, to be able to cross cell-membranes to exert its action also in the targeted organs, tissues. Therefore relatively simple, inorganic compounds are not adequate for this purpose.

The product design may follow three different routes:

a. The NO-donor prodrugs contain the —NO-group, which is released either directly by a metabolic process or after removing by enzymatic hydrolysis of some protecting group. These processes are bound largely to the liver (e.g. Molsidomine).

The sydnonimine-type prodrugs (e.g. Molsidomine) depend on the liver to remove the protecting ethoxycarbonyl-group from the molecule to produce first SIN-1 and then (in a second, pH dependent process catalysed by OH$^-$ ions) the very instable SIN-1A is formed which independently of the pH spontaneously decomposes with the release of NO.

b. Preparation of adducts or complexes of nitric oxide with various nucleophiles.

Generally the synthesis of the secondary amine NO complexes is as follows: The secondary amine e.g. anhydrous diethylamine is dissolved in anhydrous ether, oxygen is removed from the system by using aceton dry-ice bath and dry NO is bubbled through the ether solution at −78° C. for 3 hours, preferably at high pressure (100 psi).

The half-life of the prior art diethylamine-nitric oxide adduct Et$_2$—N—NH—(ONa)—N=O (DEANO) amounts to about 2 minutes, while the nitric oxide addition product of polyamine-spermine (SPNO) has a half-life of 39 minutes.

c. The prodrug is stabilized by cyclodextrin inclusion-complex formation while NO is released spontaneously under physiological conditions. The known cyclodextrin complexed prodrug is stable in the solid state.

It is known, that SIN-1 is a stable compound in solid state, however, its open-chain tautomeric form SIN-1A is extremely unstable. It is highly difficult to isolate the yellow crystalline product in pure form and it can be stored only at −80° C., under nitrogen. The SIN-1A form rapidly releases one mole NO in solid state through photolysis, and in aqueous solution even in darkness it is converted to cyanomethylene-amino-morpholine (SIN-1C).

SIN-1 is thus considered to be a prodrug and SIN-1C a biologically inactive degradation product. The equilibrium between the stable SIN-1 and the active SIN-1A (which is the real drug) depends on ambient factors (pH, temperature). However because of the extreme instability of SIN-1A— especially to oxygen—it is practically a short-lived intermediate in the decomposition process of SIN-1.

Presently SIN-1 is marketed only for intravenous administration in powder-ampoules, to be dissolved before injection. The orally administered SIN-1 prodrug is ineffective, because the hydrolytic step which is required for the formation of the NO generating SIN-1A form can not take place under acidic pH conditions, and before absorption it is rapidly and completely decomposed to SIN-1C at the higher pH of the gastro-intestinal tract.

It is also public, that SIN-1 can be stabilized by CD complexation and the equilibrium SIN-1→SIN-1A→SIN-1C can be shifted by means of complexation with cyclodextrin derivatives (PCT Publication WO 91/14681). It was disclosed that complexation with certain CD derivatives inhibit SIN-1C formation. Thus more stable complexes of SIN-1/CDPSI including those containing an increased amount of SIN-1A (showing biological activity based on higher NO release) were prepared by short time heat-treatment of the SIN-1/CDPSI complex product obtained by lyophilisation. Similarly a SIN-1/DIMEB complex was exemplified. These CD derivatives were proposed to be used in pharmaceuticals.

This document disclosed SIN-1/CD complexes or SIN-1/lactose mixture with 4,5% (w/w) SIN-1 content where the SIN-1A content in the obtained products were as follows:

| | |
|---|---|
| in CDPSI complex | 1.27% |
| in βCD complex | 0.08% |
| in DIMEB complex | 0.06% |
| in HPBCD complex | 0.115% |
| in mixture with lactose | 0.00% |

Practically complete conversion of SIN-1 to SIN-1A was not disclosed to take place even when complexation was brought about with CDPSI which was disclosed to be the most effective complexation agent for this purpose.

Moreover: CDPSI and DIMEB are not approved to be used in pharmaceuticals as yet. Thus the preparation of a stable, marketable form of pure SIN-1A is an unsolved problem.

Because SIN-1 can be applied only intravenously, its prodrug Molsidomin is used for the oral treatment of heart insufficiency: Molsidomin is hydrolysed enzymatically in the liver to SIN-1.

It was the ultimate goal of this invention to stabilize the NO-donor SIN-1A so as to ensure a formulation which can be administered both orally and parenterally, the innocuousness of which is supported with complete (even i.v.) toxicological documentation. Presently two types of cyclodextrins fulfill this fundamental requirement: gammaCD and HPβCD.

Though the SIN-1A stabilizing effect of CDPSI and DIMEB in aqueous solutions is known it does not however follow, that also the non-ionic gammaCD is effective in this respect, particularly because of its much wider cavity diameter. The excellent stabilizing effect of CDPSI has been attributed to its polymeric structure, i.e. to the cooperative effects of various cyclodextrin rings anchored in sterical vicinity.

The subjects of this invention are new SIN-1A inclusion complexes which are stable in their solid state formed of SIN-1A and cyclodextrins or cyclodextrin derivatives and releasing nitric oxide at room temperature upon dissolving in water or aqueous systems and optionally also containing an ion as a catalyst or stabilizer.

According to a preferred embodiment they contain a physiologically acceptable anion as a catalyst or stabilizer such as carboxylic acid anions i.a. acetate, formiate, propionate, ascorbinate, tartarate and/or lactate and/or inorganic acid anions such as phosphate, phosphite, borate, carbonate, hydrocarbonate, sulfate and/or sulfite. Acetate was found to be an excellent anion for the purpose. The anions may be present as salts and the corresponding cations may be preferably ammonium or alkali ions however other cations may be used as well.

As cyclodextrin component they contain βCD, gammaCD or αCD, especially for pharmaceutical use. They also may contain cyclodextrin derivatives namely hydroxypropylated or methylated cyclodextrins such as HPβCD, DIMEB, RAMEB, TRIMEB or CDPSI.

Another feature of the invention are biologically active compositions containing as their active ingredient the new SIN-1A/ cyclodextrin complexes along with auxiliary and additive ingredients facilitating their use. These include but are not limited to pharmaceutical compositions containing as an active ingredient SIN-1A inclusion complexes optionally with usual auxiliary and additional materials used in pharmaceuticals for oral, parenteral or other medical uses. The formulations are preferably powders dissolved directly before medication takes place. Thus the parenteral formulations are preferably powders dissolved prior to injection.

Pharmaceutical compositions of preference are those containing as an active ingredient SIN-1A inclusion complexes which are stable in their solid state and which are formed with βCD, gammaCD or αCD and containing a physiologically acceptable anion as a catalyst or stabilizer, such as carboxylic acid anions including acetate, formiate, propionate, ascorbinate, tartarate and/or lactate and/or inorganic acid anions comprising phosphate, phosphite, borate, carbonate, hydrocarbonate, sulfate and/or sulfite. The anions may be optionally in the form of their salts e.g. the ammonium or alkali salts. Ammonium acetate is a preferred salt for the purpose.

Further objects of the present invention are kits to be used as NO-liberating standards to release NO in a predictable amount and rate on dissolving in aqueous media containing as an active ingredient SIN-1A inclusion complexes according to the present invention.

This is possible because the present invention relates to the preparation and stabilization of the extremely labile SIN-1A, which when released from the cyclodextrin cavity—even after simple dissolving in distilled water—immediately generates the NO in a predictable amount and rate without the need of any further enzyme or reactant.

The present invention includes processes for the preparation of new SIN-1A inclusion complexes which are stable in their solid state and which are formed with cyclodextrins or with cyclodextrin derivatives by way of subjecting at a suitable pH SIN-1 to the catalytic action of ions to shift the equilibrium towards formation of SIN-1A in the presence of cyclodextrins or cyclodextrin derivatives capable to form inclusion complexes, whereby the SIN-1A formed is immediately complexed and stabilized by formation of SIN-1A/ cyclodextrin inclusion complexes. The process includes isolating in the solid state the obtained SIN-1A/CD complexes optionally containing the ions. The ions may be contained in the form of their salts.

It is a preferred process according to the invention to react SIN-1 and a cyclodextrin or cyclodextrin derivative in the solid state in the presence of an ion preferably in the form of its salt as a catalyst by thoroughly admixing or milling the components together. Another route according to the invention follows freeze drying an aqueous, oxygen-free solution containing the components, followed preferably by "second drying" in vacuo.

It is preferred to use ammonium or alkali salts formed with carboxylic acid anions such as acetate, formiate, propionate, ascorbinate, tartarate and/or lactate and/or inorganic acid anions such as borate, carbonate, hydrocarbonate, phosphate, phosphite, sulfate, and/or sulfite as catalyst of the process. The salts used may contain volatile anions or cations which are eliminated partly or totally during the process such as ammonium or carbonate ions.

When accomplishing the above it is advantageous to carry out the reaction at pH values between 6 to 10 and—when water was used as a reaction medium—applying "second drying" at 40° to 100° C. preferably 50°–70° C.

As it is seen from the NO-release tests, SIN-1A/ cyclodextrin complexes immediately produce nitric oxide after dissolution of the solid complexes in aqueous systems. Thus one way to obtain a SIN-1A cyclodextrin complex of controlled composition (having the lowest SIN-1C content) consists in tautomerization of SIN-1 and the simultaneous complexation of the formed SIN-1A in solid state.

The situation is similar when the complex preparation is performed by freeze-drying. In this case the second-drying step (following lyophilization) is able to ensure the conditions for the solid-state catalytic complex formation.

Another subject of the invention consists in methods of nitric oxide treatment of living cells. This includes but is not limited to the treatment of nitric oxide dependent symptoms in humans or animals like anginic and ischemic heart failures, physiological control of blood pressure, platelet aggregation, mediation of relaxation of peristalsis, penile erection and others. This is accomplished by administering preferably in oral or parenteral application to the patients in need of such treatment an effective amount of a new SIN-1A inclusion complex which is stable in its solid state and which is formed with cyclodextrins or with cyclodextrin derivatives and which contains at least one ion as a catalyst or stabilizer and which upon dissolving in water or aqueous systems at room temperature releases nitric oxide.

The preferred embodiment relies in administering the complexes of SIN-1A formed with βCD, gammaCD or αCD and containing optionally in the form of their ammonium or alkali salts carboxylic acid anions such as acetate, formiate, propionate, ascorbinate, tartarate and/or lactate and/or inorganic acid anions such as phosphate, phosphite, borate, carbonate, hydrocarbonate, sulfate and/or sulfite.

The invention includes the method of treatment of nitric oxide dependent symptoms in humans or animals by treating the patient with the product of the quantitative conversion of SIN-1 into SIN-1A accomplished by way of an ion- catalysed and cyclodextrin-stabilized solid state conversion in the presence of a cyclodextrin or a cyclodextrin derivative capable to immediately form inclusion complexes.

The major advantages of SIN-1A/CD complexes as compared with SIN-1 or other NO -donors known hitherto are thus the following:

stability at the long term,
rapidity of action,
increased half-life,
independence from the liver,
independence from the pH,
eventually a greater ability to reach their targets (tissues).

Having the stable composition in hands makes it possible to open a new phase for treatments with nitric oxide which is called by some authors as "biochemistry's unexpected new superstar" (Chem. Ing. News Dec.1993.page 26–38).

The following Examples serve illustration and not limitation of the invention.

I. CHEMICAL EXAMPLES

Example I.1

Preparation of SIN-1A/gammaCD Complex 2 g of gammaCD and 0.8 g of ammonium acetate were dissolved in 25 ml of distilled water by ultrasonication. The solution was deoxygenated by bubbling with helium gas, thereafter 200 mg of SIN- 1 substance were dissolved. The solution was immediately freeze-dried for isolation of the solid complex. Second drying at 40°–50° C. for 2 hours was applied to remove the water content of the complex almost completely. Both solution and the substance were protected from light. The complex is a light yellow powder. Yield: 2.6±0.1 g Loss on drying is less than 1%.

| HPLC analysis: | SIN-1 content: | not detectable |
|---|---|---|
| | SIN-1A content: | 11.7 ± 0.2% |
| | SIN-1C content: | 0.36 ± 0.1% |

In all examples of this document the following method was used for simultaneous determination of SIN-1, SIN-1A and SIN-1C by HPLC:

Column: Ultrasphere, I.P. analytical column (Beckman-Astec) 4.6±250 mm, particle size 5 μm.

| Mobile phase: | 0.01 M phosphate buffer pH = 6.0 | 800 ml |
|---|---|---|
| | tetrahydrofuran | 200 ml |
| | sodium-1-dodecanesulfonate | 0.405 g/dm$^3$ |

Ionic strength: 0.05 gion/dm$^3$ (corrected with sodium sulphate)

Flow rate: 1 ml/min., p=190 bar. Sample size: 20 μl
Wavelength of detection:
–230 nm BW: 6 (ref. 350 nm BW: 80) for SIN-1A and SIN-1C between 0–8 minutes
–292 nm BW: 6 (ref. 400 nm BW:80) for SIN-1 after 8 minutes

| Retention times: | SIN-1 | 9.6 min. |
|---|---|---|
| | SIN-1C | 4.5 min. |
| | SIN-1A | 4.8 min. |

Calibration was performed with freshly prepared SIN-1 and SIN-1C solutions. SIN-1A content was expressed in SIN-1C equivalent.

Example I.2

Preparation of SIN-1A/βCD Complex 16 g of βCD (water content 14%) and 7 g of ammonium acetate were dissolved in 1000 ml of distilled water by ultrasonication. The solution was deoxygenated by bubbling with helium gas, thereafter 3 g of SIN-1 substance were dissolved. The solid complex was isolated by immediate freeze-drying and water content was removed at 40°–50° C. Both solution and substance were protected from light. The complex is a yellowish very light powder. Yield: 20±1 g. Loss on drying <1%

| HPLC analysis: | SIN-1 content: | not detectable |
|---|---|---|
| | SIN-1A content: | 12 ± 1% |
| | SIN-1C content: | 0.30 ± 0.2% |

Example I.3

Preparation of SIN-1A/HPBCD Complex 2 g of HPBCD (DS=2.8) and 0.8 g of ammonium acetate were dissolved in 25 ml of distilled water by ultrasonication. On deoxygenation by bubbling with helium gas, 200 mg of SIN-1 were dissolved. The solid complex solution was isolated by immediate freeze-drying. The water content was removed at 40°–50° C. Both solution and substance were protected from light. 2,8±0,1 g of SIN-1A/HPBCD complex as a light yellow powder were obtained. Loss on drying <1%.

| HPLC analysis: | SIN-1: | not detectable |
|---|---|---|
| | SIN-1A: | 11.6 ± 0.2% |
| | SIN-1C: | 0.36 ± 0.1%. |

Example I.4

Preparation of SIN-1A/RAMEB Complex 2 g of RAMEB (DS=1,8) and 0,8 g of ammonium acetate were dissolved in 25 ml of distilled water by ultrasonication. On deoxygenation by bubbling with helium gas 200 mg of SIN-1 substance were dissolved, the solution was freeze-dried and the isolated solid complex dried at 40°–50° C. for 2 hours. Solution and substance were protected from light. 2.8±0,1 g SIN-1A RAMEB complex were obtained as a light yellow powder. Loss on drying <1%

| HPLC anaiysis: | SIN-1: | not detectable |
|---|---|---|
| | SIN-1A: | 12.0 ± 0.2% |
| | SIN-1C: | 0.6 ± 0.1%. |

Example I.5.

Preparation of SIN-1A βCD Complex in Phosphate Buffer Solution 1 g of βCD (water content: 14%) was dissolved in 55 ml of a pH=8.0 phosphate buffer solution according to USP XXII by ultrasonication. On deoxygenation with helium gas 100 mg of SIN-1 were dissolved. The solution was immediately freeze-dried. Solution and substance were protected from light. 1±0.1 g of SIN-1A/βCD were obtained as a yellowish coloured very light powder. Loss on drying <1%

| HPLC analysis: | SIN-1 content: | not detectable |
|---|---|---|
| | SIN-1A content: | 8.3% |
| | SIN-1C content: | 0.24% |

Example I.6

1 g of βCD (water content 14%), 100 mg of SIN-1 hydrochloride and 100 mg of ammonium acetate were thoroughly mixed in a mortar for 15 minutes. After a short time of rubbing the mixture became visibly yellow. After 2 days of storage in a closed container protected from light, HPLC analysis according to Example I.1 was taken to give the following results:

SIN-1 content: not detectable
SIN-1A content: 7.9±0.2%
SIN-1C content: 0.41±0.1%

Example I.7

Using the process of Example I.6. but taking 50 mg of ammonium acetate the visible formation of SIN-1A (yellow coloration) is slower, it took several hours. HPLC analysis of the SIN-1A/βCD after 2 days of storage:

SIN-1 0.5±0.1%
SIN-1A 6.9±0.2%
SIN-1C 0.6±0.1%

Example I.8

Following the procedure as described in Example I.6. but applying 300 mg of ammonium acetate the yellow coloration of the mixture occurs practically immediately after mixing the components.

HPLC analysis of the βCD complex same day after preparation:

SIN-1: not detectable
SIN-1A: 6.9±0.2%
SIN-1C: 0.5±0.1%

Example I.9

1 g of βCD (water content 14%), 100 mg of SIN-1 hyrochloride and 100 mg of sodium acetate.3H$_2$O were thoroughly mixed in a mortar for 15 minutes, followed by heat treatment of the mixture at 70° C. for 1 hour.

HPLC analysis of the heat-treated sample:

SIN-1: not detectable
SIN-1A: 7.1±0.2%
SIN-1C: 0.8±0.1%

II. COMPARATIVE EXAMPLES

Example II.1

Attempted preparation of SIN-1A/βCD with acetic acid Preparation was carried out as in Example I.2 but instead of water and ammonium acetate the βCD was dissolved in a 0.1 mole acetic acid solution.

| HPLC analysis of the product: | SIN-1: | 8.4% |
|---|---|---|
| | SIN-1A: | 0.28% |
| | SIN-1C: | not detectable. |

Thus the solid SIN-1A/βCD complex was not isolated.

Example II.2

Attempted preparation of SIN-1A/βCD with sodium hydroxide Complexation was carried out as described in Example I.5, but the βCD was dissolved in 55 ml of pH 8.4 aqueous sodium hydroxide istead of using ammonium acetate. HPLC analysis of the obtained solid product:

SIN-1: 10.5%
SIN-1A: 0.40%
SIN-1C: not detectable.
No SIN-1A/βCD complex was isolated.

III. ANALYTICAL AND BIOLOGICAL EXAMPLES

Example III.1

The effectivity of conversion and stability of the SIN-1A complexes are illustrated by Table 1. The samples were stored at room temperature for 11 months in glass containers under air atmosphere, protected from light. The SIN-1A content is given in SIN-1C equivalent.

TABLE 1

| | SIN-1 content % | | SIN-1A content % | | SIN-1C content % | |
|---|---|---|---|---|---|---|
| | after preparation | after storing for 11 months | after preparation | after storing for 11 months | after preparation | after storing for 11 months |
| SIN-1/αCD | 3.59 | | 2.46 | | 0.68 | |
| SIN-1/βCD | 0 | 0 | 10.66 | 9.59 | 0.68 | 0.50 |
| SIN-1/γCD | 0 | 0 | 11.71 | 7.23 | 0.32 | 0.49 |
| SIN-1/HPBCD | 0.03 | 0 | 11.61 | 7.53 | 0.36 | 0.39 |
| SIN-1/RAMEB | 0 | 0 | 12.11 | 9.43 | 0.68 | 0.87 |

Example III.2

A SIN-1A/βCD sample contained immediately after preparation 11.47% SIN-1A. When stored at room temperature for 12 months it contained 8.36% SIN-1A, and after 23 months it contained 6.59% SIN-1A. The SIN-1C contents were 0.18, 1.31 and 1.57% respectively.

The complexes contained approx. 5–8% inclusion water, mainly bound to the cyclodextrin cavity.

Example III.3

The stability enhancing effect of heat-treatment ("second drying") after freeze-drying is illustrated by Table 2.

TABLE 2

| | SIN-1 content % | | SIN-1A content % | | SIN-1C content % | |
|---|---|---|---|---|---|---|
| SIN-1/βCD | after preparation | after storing for 11 months | after preparation | after storing for 11 months | after preparation | after storing for 11 months |
| SIN-1/βCD | 0 | 0 | 12.7 | 10.89 | 0.40 | 0.79 |
| SIN-1/βCD heat treated | 0 | 0 | 12.7 | 12.50 | 0.40 | 0.56 |

TABLE 2-continued

| | after prepa- ration | after storing for 19 months | after prepa- ration | after storing for 19 months | after prepa- ration | after storing for 19 months |
|---|---|---|---|---|---|---|
| SIN-1/βCD | 0.04 | 0 | 14.81 | 7.41 | 0.29 | 1.75 |
| SIN-1/βCD heat treated | 0.04 | 0 | 14.81 | 12.41 | 0.29 | 1.15 |

EXAMPLE III.4

Rate and extent of NO release from SIN-1A/βCD complex. Release of NO in SIN-1A/CD solutions was examined by chemical and biological methods.

250 mg of complex (corresponds to approximately 25 mg of SIN-1A) were dissolved in 100 ml of distilled water. Right after dissolution liberation of NO was indirectly detected by simultaneously measuring decrease of the SIN-1A content and formation of the SIN-1C metabolite by HPLC as a function of time. The measurements were repeated in different time intervals, while protecting from light.

Table 3 illustrates the kinetics of decomposition of SIN-1A in distilled water at room temperature in presence of βCD, gammaCD and HPBCD.

TABLE 3

| | βCD complex | | γCD complex | | HPBCD complex | |
|---|---|---|---|---|---|---|
| time, min. | SIN-1A µg/ml | SIN-1C µg/ml | SIN-1A µg/ml | SIN-1C µg/ml | SIN-1A µg/ml | SIN-1C µg/ml |
| 0 | 213 | 13 | 270 | 7 | 240 | 8 |
| 20 | 152 | 39 | — | — | — | — |
| 40 | 116 | 53 | — | — | — | — |
| 50 | 104 | 59 | 165 | 46 | 135 | 52 |
| 70 | 86 | 65 | — | — | — | — |
| 100 | 55 | 75 | 140 | 58 | 92 | 70 |
| 130 | 40 | 86 | — | — | 80 | 140 |
| 180 | 19 | 95 | 95 | 75 | — | — |

The estimated $T_{1/2}$ (half-life) of the complexes calculated from the decrease of SIN-1A content are 53 min. for βCD, 24 min. for gammaCD and 70 min. for HPBCD.

Example III.5

Release of NO in a more diluted SIN-1A/βCD solution (100 µg/ml of SIN-1A/βCD complex corresponds to 10 µg/ml of SIN-1A) was detected by UV-spectrophotometry measuring the formation of SIN-1C metabolite as a function of time. SIN-1A→SIN-1C transition is accompanied by a very characteristic UV-spectrum change, as SIN-1A has an UV maximum at 230±1 nm and shows no absorbance at $\lambda_{max}$ SIN-1C at 277±1 nm.

10 mg of the SIN-1A/βCD complex (corresponds to approximately 1 mg of SIN-1A) were dissolved in 100 ml of distilled water. UV-spectrum of the solution was registered between 200-350 nm without dilution immediately after dissolution and registration was repeated in different time intervals, protected from light. The formed SIN-1C amount was calculated from the absorbance values at 277±1 nm using the calibration curve taken with a SIN-1C standard. SIN-1C concentration was less than 0.7 µg/ml right after dissolution and about 7.8 µg/ml after 270 minutes. Presumably the equivalent amount of NO was released. Estimated half-life of the complex: 90–100 minutes.

FIG. 1. illustrates how the UV spectra change as a function of time: UV spectra of a SIN 1A/βCD complex at 10 minute time intervals up to 160 minutes after dissolution of 10 mg of the complex in 100 ml of distilled water are shown. Absorbance is spotted against wavelength.

Example III.6

Formation of NO was determined directly, using NO specific porphyrinic microsensor detection. The method (Nature, Vol. 358 p. 675, 1992) is able to monitor the NO release up to 10–20 moles, in a single cell in biological microsystems in amperometric or voltametric mode.

In a pH=7.4 phosphate buffer at 37° C. 1 mM SIN-1A/βCD released NO at a rate of 2.37 µM/min. in the first 5 minutes, and between the 10th and 30th minute at a rate of 0.17 µM/min. Dissolving 0.1 mM of substance the relevant values were 0.42 µM and 0.07 µM respectively.

Example III.7

Inhibition of platelet aggregation by SIN-1A/βCD complex: Nitric oxide had been identified as a natural messenger molecule in the inhibition of platelet aggregation via the guanylate-cyclase/cyclic GMP system (Blood, 57, 946, 1981). We studied the biological effects of SIN-1 and SIN-1A/βCD complex by comparing their platelet aggregation inhibiting effects. The platelet aggregation was studied in rabbit and human platelet rich plasma (J. Cardiovasc. Pharmacol. 14 suppl. 11; page 120, 1989). In each batch of platelet rich rabbit plasma 8 dose response curves were registered with the thromboxane mimetic U-46619 (0.25–4.0 µM) in the presence of 0, $10^{-7}$, $10^{-6}$ or $10^{-5}$ moles of SIN-1A/βCD complex. The dose response curves were performed in random sequence. Thereafter a fixed concentration of U46619 (4 µM) was used to make full concentration-inhibition curves to SIN-1 and to SIN-1A/βCD. U46619 induced a concentration-related aggregation. The aggregation inhibiting effect of SIN-1A/βCD complex at identical molar concentration in all cases was significantly higher than that of SIN-1. The $pD_2$ (negative logarithm of concentration producing 50% inhibition) values were 5.57±0.11 (n=7) for SIN-1 and 6.36±0.07 (n=7) for SIN-1A/βCD complex, indicating that the complex was about 6-fold more potent than SIN-1 in this test.

In some similar experiments the SIN-1A/βCD complex was found to be about 10-fold as potent as SIN-1.

Example III.8

The experiments described in Example III.7 were repeated using human citrate platelet rich plasma with SIN-1, freshly prepared SIN-1A/βCD complex (SIN-1A content 14.8%) and with a SIN-1A/βCD complex, that has been stored at room temperature for 23 months (SIN-1 content originally was 11.47%, after 23 months it was 6.59%). Table 4 illustrates the results showing the negative logarithms of the concentration ($pD_2$) of SIN-1 and SIN-1A βCD complex causing 50% inhibition of U46610 induced aggregation in human platelet rich plasma.

Both amplitude and slope of the aggregation curve were evaluated. The difference in the $pD_2$ values indicate that freshly prepared SIN-1A/βCD was about 8-fold more potent than SIN-1. The complex stored for 23 months was found to be 3-fold less active than the freshly prepared complex, but 3-fold more potent than SIN-1 itself.

TABLE 4

| Substance | | aggregation | |
|---|---|---|---|
|  | n | amplitude | slope |
| SIN-1 | 10 | 4.8 ± 0.05 | 4.85 ± 0.13 |
| SIN-1A βCD freshly prepared (SIN-1A content: 14.81%) | 10 | 5.54 ± 0.10 | 5.85 ± 0.11 |
| SIN-1A βCD (stored for 23 months, SIN-1A content: 6.59%) | 3 | 5.80 ± 0.16 | 5.42 ± 0.06 |

The results of in vivo tests suggest that the SIN-1A/βCD complexes disclosed here are useful inhibitors of platelet aggregation iv vivo.

As is reflected from the half-life values, SIN-1A/ cyclodextrin complexes are able to continuously produce nitric oxide generation at a more nearly constant rate for much longer time after administration.

Example III.9

Commercially available SIN-1 (CORVASAL) was compared with the SIN-1A/βCD complex on carotid artery of rabbits. The carotid artery of nembutal anesthesized rabbits was dissected free, 3 mm long rings were immobilized in a clamp and placed in the organ baths. Contraction was induced with phenylephrine $3 \times 10^{-7}$M three times with following rinsing. The dose response curves were registered for $3 \times 10^{-9}$M to $3 \times 10^{-5}$M CORVASAL (referred to SIN-1 content) and for $3 \times 10^{-9}$ to $3 \times 10^{-5}$ moles SIN-1A/βCD (referred to SIN-1A content).

Figure 2:
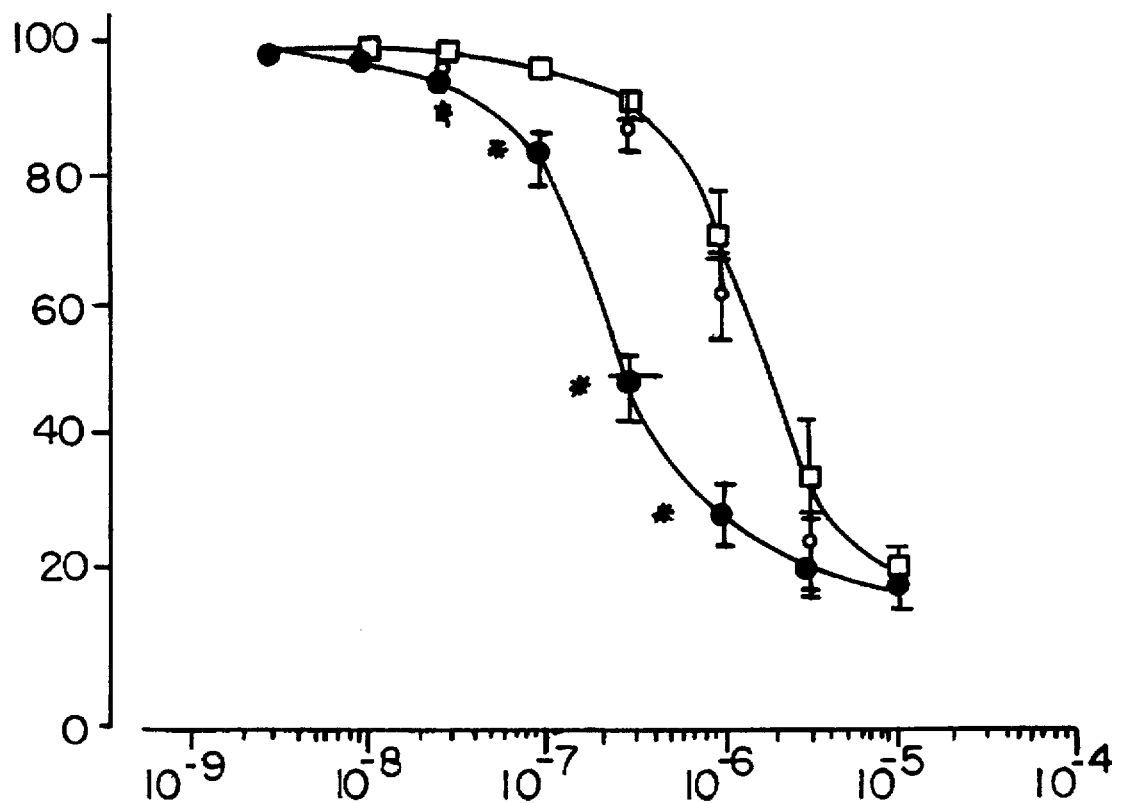

FIG. 2. shows the contraction versus drug concentration curve. As it is seen, the βCD complexed SIN-1A drug was about 6-fold more effective than free SIN-1. The illustrated points represent the average of 6 measurements.

We claim:

1. A solid inclusion complex which is stable in its solid state consisting of N-morpholino-N-nitrosaminoacetonitrile and βCD, gamma CD or αCD cycledextrins or their hyroxy-propylated or methylated derivatives also containing anions as a catalyst or stabilizer and cations, wherein said inclusion complex does not contain 3-morpholino-syndonimine and no more than about 0.7% of cyanomethylene-amino morpholine.

2. An inclusion complex according to claim 1, wherein said anions are in the form of a salt.

3. A kit for the release of NO in a predictable amount and rate on dissolving in aqueous media containing as an active ingredient a solid N-morpholino-N-nitrosaminoacetonitrile inclusion complex according to claim 1.

4. An inclusion complex according to claim 1, said anions being selected from the group consisting of acetate, formate, propionate, ascorbate, tartrate, lactate, phosphate, phosphite, borate, carbonate, hydrocarbonate, sulfate and sulfite, and said cations being selected from the group consisting of sodium and ammonium.

5. An N-morpholino-N-nitrosaminoacetonitrile inclusion complex according to claim 1 consisting of hydroxy-propylated or methylated cyclodextrin derivatives selected from the group consisting of hydroxypropyl-β-cyclodextrin, heptakis-2,6-di-O-methyl-β-cyclodextrin, randomly methylated β-cyclodextrin or heptakis 2, 3,6-tri-O-metyl-β-cyclodextrin.

6. A pharmaceutical composition comprising as an active ingredient a solid inclusion complex according to claim 1 and a physiologically acceptable anion as a catalyst or stabilizer in the form of a salt and a pharmaceutically acceptable carrier.

7. A pharmaceutical composition comprising as an active ingredient a solid N-morpholino-N-nitrosaminoacetonitrile inclusion complex which is stable in their solid state and which is formed with βCD, gammaCD or αCD and as a catalyst or stabilizer, a physiologically acceptable salt selected from the group consisting of ammonium acetate, alkali acetates, ammonium carbonate, ammonium hydrocarbonate, alkali carbonates and alkali hydrocarbonates.

8. The pharmaceutical composition of claim 7, wherein said physiologically acceptable salt is selected from the group consisting of ammonium acetate and alkali acetates.

9. Process for the preparation of a solid N-morpholino-N-nitrosamino-acetonitrile (SIN-1A) inclusion complex which is stable in its solid state and which is formed with cyclodextrins or with cyclodextrin derivatives, said process comprising reacting at a suitable pH 3-morpholino-sydnonimine (SIN-1) with a salt as catalyst, said salt containing organic anions selected from the group consisting of acetate, formate, propionate, ascorbate, tartrate and lactate, and inorganic acid anions selected from the group consisting of phosphate, phosphite, borate, carbonate, hydrocarbonate, sulfate, sulfite, and cations selected from the group consisting of sodium and ammonium to the catalytic action of ions to shift the equilibrium towards formation of N-morpholino-N-nitrosaminoacetonitrile in the presence of βCD, gamma CD or αCD cyclodextrins or their hydroxy-propylated or methylated derivatives, whereby the N-morpholino-N-nitrosaminoacetonitrile formed is immediately complexed and stabilized by formation of a N-morpholino-N-nitrosaminoacetonitrile cyclodextrin inclusion complex and isolating in the solid state the obtained N-morpholino-N-nitrosaminoacetonitrile CD complex.

10. A process according to claim 9 comprising reacting 3-morpholino-sydnonimine and βCD, gamma CD or αCD or their hydroxy-propylated or methylated derivatives in the solid state in the presence of an ion optionally in the form of its salt as a catalyst by thoroughly admixing or milling the components together or by freeze drying an aqueous, oxygen-free solution containing the components.

11. A process according to claim 9 said process comprising a catalysis process comprising catalysts or stabilizers selected from the group consisting of ammonium or alkali salts formed with organic anions selected from the group consisting of acetate, formate, propionate, ascorbate, tartrate and lactate and inorganic acid anions selected from the group consisting of borate, carbonate, hydrocarbonate, phosphate, phosphite, sulfate and sulfite.

12. A process according to claim 9, said step of reacting occurring at a pH value of between 6 to 10.

13. The process of claim 9, said process occurring in a water medium, said process further comprising a step of second drying at 40° to 100° C.

14. The process of claim 10, said process further comprising the step of second drying.

15. Method of nitric oxide treatment of living cells selected from the group consisting of nitric oxide dependent symptoms of human or animal anginic heart failure, ischemic heart failure, physiological control of blood pressure, platelet aggregation, mediation of relaxation of peristalsis, and penile erection comprising administering to patients in need of such treatment an effective amount of a solid N-morpholino-N-nitrosaminoacetonitrile inclusion complex which is stable in its solid state and which is formed with βCD, gammaCD, or αCD cyclodextrins or their hydroxy-propylated or methylated derivatives, and as a stabilizer or catalyst a salt containing ammonium or alkali cations and organic anions selected from the group consisting of acetate, formate, propionate, ascorbate, tartrate and lactate, and inorganic acid anions selected from the group consisting of phosphate, phosphite, carbonate, hydrocarbonate, and sulfate.

16. Method of treatment of nitric oxide dependent symptoms in living cells according to claim 15 comprising administering an effective amount of the complexes of SIN-1A formed with βCD, gammaCD or αCD and containing in the form of their ammonium or alkali salts, organic anions selected from the group consisting of acetate, formate, propionate, ascorbate, tartrate, and lactate and inorganic acid anions such as phosphate, phosphite, carbonate, hydrocarbonate, and sulfate, optionally in the form of a pharmaceutical composition.

17. Method of treatment of nitric oxide dependent symptoms in humans or animals comprising administering to the patient in need of such treatment an effective amount of the product of the quantitative conversion of SIN-1 into SIN-1A accomplished by way of an ion-catalysed and cyclodextrin-stabilized solid state conversion in the presence of a cyclodextrin or cyclodextrin derivative capable of immediately forming an inclusion complex.

18. The method of claim 13, wherein said step of administering is selected from the group consisting of oral and parenteral administration.

19. The method of claim 14, wherein said living cells are selected from the group consisting of animal cells and human cells.

* * * * *